US00PP10970P

United States Patent [19]

van Rijn

[11] Patent Number: Plant 10,970

[45] Date of Patent: Jun. 22, 1999

[54] ANTHURIUM PLANT NAMED 'EVELINE'

[75] Inventor: Magdalena J. M. van Rijn, Schipluiden, Netherlands

[73] Assignee: Rijnplant B.V., Schipluiden, Netherlands

[21] Appl. No.: 09/006,828

[22] Filed: Jan. 14, 1998

[51] Int. Cl.[6] ..... A01H 5/00

[52] U.S. Cl. ..... Plt./369

[58] Field of Search ..... Plt./365, 367, 368, Plt./369

[56] References Cited

U.S. PATENT DOCUMENTS

P.P. 9,704 11/1996 van Rijn ..... Plt./367

*Primary Examiner*—Lynette R. F. Smith
*Assistant Examiner*—Kent L. Bell
*Attorney, Agent, or Firm*—C. A. Whealy

[57] ABSTRACT

A distinct cultivar of Anthurium plant named 'Eveline', characterized by its tall, upright, outwardly arching and freely branching growth habit; large glossy dark green leaves that are cordate in shape; long and thick petioles; numerous inflorescences that are positioned high above the foliage on long, strong, and erect scapes; large red spathes with auriculate base; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name 'Eveline'.

The new Anthurium is a product of a planned breeding program conducted by the inventor in Schipluiden, The Netherlands. The objective of the program is to create new Anthurium cultivars that have a freely branching growth habit, strong plant growth, medium leaf size, rapid growth rate, strong roots, attractive spathe color, numerous inflorescences and good post-production longevity. The new cultivar originated from a self-pollination by the inventor in 1992 of the inventor's proprietary *Anthurium andreanum* selection code number 924. The cultivar 'Eveline' was discovered and selected by the inventor as a plant within the progeny of the stated cross in a controlled environment in Schipluiden, The Netherlands.

Asexual propagation by tissue culture of the new cultivar at Schipluiden, The Netherlands, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of 'Eveline'. These characteristics in combination distinguish 'Eveline' as a new and distinct cultivar:

1. Tall, upright, outwardly arching and freely branching growth habit.

2. Large glossy dark green leaves that are cordate in shape.

3. Long and thick petioles.

4. Numerous inflorescences that are positioned high above the foliage on long, strong, and erect scapes.

5. Large red spathes with auriculate base.

6. Good post-production longevity.

The new Anthurium can be compared to its parent cultivar, the proprietary selection code number 924. Plants of the new Anthurium are different from plants of selection code number 924 in the following characteristics:

1. Plants of the cultivar 'Eveline' have more flexible leaves than plants of the selection code number 924.

2. Plants of the cultivar 'Eveline' have much larger spathes than plants of the selection code number 924.

3. Plants of the cultivar 'Eveline' have red spathes whereas plants of the selection code number 924 have pink spathes.

The new Anthurium can also be compared to plants of its sibling, the cultivar 'Sweet Love', disclosed in U.S. Plant Patent application Ser. No. 09/007,036. Plants of the new Anthurium are different from plants of the cultivar 'Sweet Love' in the following characteristics:

1. Plants of the new Anthurium have longer internodes and thicker stems than plants of the cultivar 'Sweet Love'.

2. Plants of the new Anthurium have larger and darker green leaves than plants of the cultivar 'Sweet Love'.

3. Plants of the new Anthurium have longer and thicker petioles than plants of the cultivar 'Sweet Love'.

4. Plants of the new Anthurium have larger spathes than plants of the cultivar 'Sweet Love'.

5. Plants of the new Anthurium have longer and thicker scapes than plants of the cultivar 'Sweet Love'.

6. Plants of the new Anthurium have red-colored spathes whereas plants of the cultivar 'Sweet Love' have salmon pink-colored spathes.

The new Anthurium can be compared to the Anthurium cultivar 'Elisabeth' disclosed in U.S. Plant Pat. No. 9,704. Plants of the new Anthurium differ from plants of the cultivar 'Elisabeth' in the following characteristics:

1. Plants of the cultivar 'Eveline' are more compact than plants of the cultivar 'Elisabeth'.

2. Plants of the cultivar 'Eveline' have smaller leaves than plants of the cultivar 'Elisabeth'.

3. Plants of the cultivar 'Eveline' are more freely branching than plants of the cultivar 'Elisabeth'.

4. Spathe color of plants of the cultivar 'Eveline' is redder than spathe color of plants of the cultivar 'Elisabeth'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical potted plant of 'Eveline'. Leaf and flower colors in the phograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Schipluiden, The Netherlands, in a glass greenhouse with an average day temperature of 25° C. and an average night temperature of 19° C.

Botanical classification: *Anthurium andreanum* cultivar 'Eveline'.

Parentage:

*Seed or female parent*.—Inventor's proprietary *Anthurium andreanum* selection code number 924.

*Pollen or male parent*.—Inventor's proprietary *Anthurium andreanum* selection code number 924.

Propagation:

*Method*.—By tissue culture.

*Time to initiate roots*.—70 and 84 days at 24° C. and 21° C. temperatures, respectively.

*Rooting habit*.—Freely branching, numerous fleshy roots.

Plant description:

*Plant shape*.—Upright, inverted triangle, symmetrical.

*Growth habit*.—Erect when young, becoming outwardly arching as leaves develop. Freely branching, bushy and dense. Appropriate for 12 to 30-cm containers.

*Plant height*.—About 110 cm from soil level to apex of spathes.

*Plant vigor*.—High.

*Growth rate*.—Moderate.

*Crop time*.—About 16 to 17 months are usually required from planting of a young plant to a finished plant.

*Stem description*.—Diameter: About 2 cm. Internode length: About 1.5 cm.

*Foliage description*.—Length: About 28 cm. Width: About 22 cm. Shape: Cordate. Apex: Apiculate. Base: Auriculate, moderate lobing, not overlapping. Margin: Entire, undulating. Texture: Leathery, Flexible, smooth, glabrous, glossy. Surface: Rugose, wavy, midvein prominent. Angle with respect to petiole: Drooping. Color: Upper surface: Darker than 137A. Lower surface: 144A/146C. Petiole: Length: About 60 cm. Diameter: About 7.5 mm. Cross-section: Rounded. Color: 144A.

Inflorescence description:

*Inflorescence arrangement*.—Spathe with spadix held above the foliage. Flowering structures arise from leaf axils. Freely flowering, numerous inflorescences per plant.

*Inflorescence longevity*.—Spathe/spadix last about six weeks under winter conditions and up to three or four months under summer conditions; inflorescences persistent.

*Flowers*.—Quantity of flowers per spadix: Numerous, about 12 flowers on the middle 2-cm portion of the spadix. Shape: Rounded. Diameter: About 1 mm.

*Spathe*.—Length: About 17 cm. Width: About 14 cm. Height above foliage: About 15 cm. Shape: Cordate. Apex: Acuminate. Base: Auriculate, deeply lobed, not overlapping. Margin: Entire, rolling inward. Texture: Leathery, glabrous, somewhat glossy. Surface: Slightly wavy. Angle with respect to scape: Perpendicular. Color: Front surface: 46C/46D. Back surface: 46D.

*Spadix*.—Length: About 7.5 cm. Diameter: About 9 mm. Shape: Columnar. Crosss section: Rounded. Longitudinal axis: Bent before flowering. Color, just before flowering: Base: Yellow. Apex: Cream white, 158A.

*Scape*.—Length: About 80 cm. Diameter: About 7.5 mm. Aspect: Strong and erect. Color: Green, 146A, with slight anthocyanin.

*Reproductive organs*.—Androecium: Pollen color: Cream white. Gynoecium: Stigma shape: Ovoid. Ovary: Protogyneous.

Disease resistance: Plants of the new Anthurium have demonstrated good tolerance to root pathogens common to Anthuriums.

Seed development: Seed development is rarely observed.

It is claimed:

1. A new and distinct cultivar of Anthurium plant named 'Eveline', as illustrated and described.

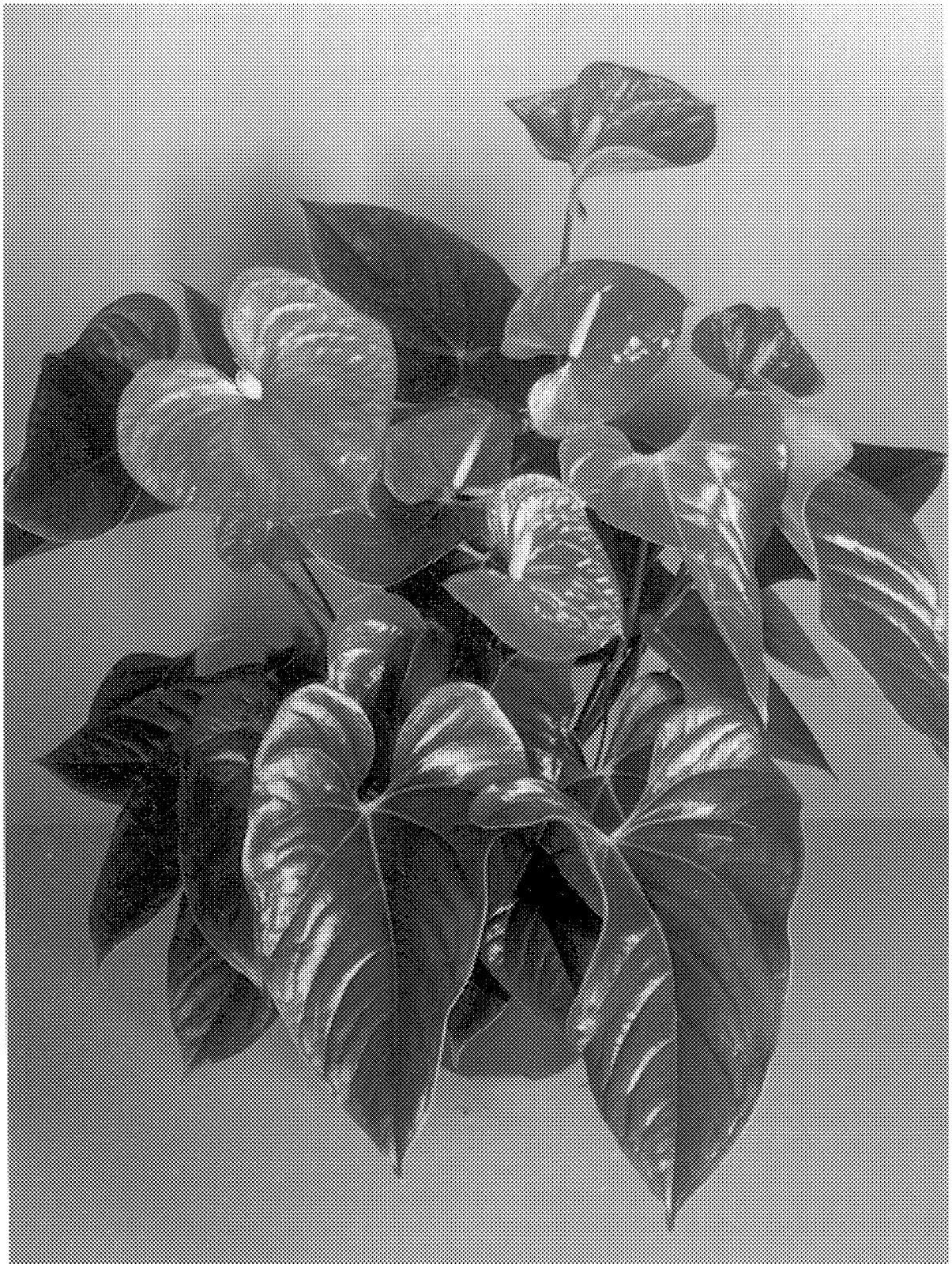

* * * * *